United States Patent
Names

(10) Patent No.: US 6,666,684 B1
(45) Date of Patent: Dec. 23, 2003

(54) IMPRESSION AND FOUNDATION SYSTEM FOR IMPLANT-SUPPORTED PROSTHESIS

(76) Inventor: Curtis D. Names, 367 Metzgar St., Half Moon Bay, CA (US) 94019

( * ) Notice: Subject to any disclaimer, the term of this patent is extended or adjusted under 35 U.S.C. 154(b) by 0 days.

(21) Appl. No.: 09/562,048

(22) Filed: May 1, 2000

Related U.S. Application Data

(63) Continuation-in-part of application No. 08/811,494, filed on Mar. 5, 1997, now Pat. No. 6,056,547.

(51) Int. Cl.$^7$ ................................................. A61C 8/00
(52) U.S. Cl. ..................... 433/173; 433/213; 433/214
(58) Field of Search ............................. 433/172, 173, 433/214, 213

(56) References Cited

U.S. PATENT DOCUMENTS

| | | | | |
|---|---|---|---|---|
| 4,775,320 A | * | 10/1988 | Marshall et al. | 433/180 |
| 5,055,047 A | * | 10/1991 | Names | 433/174 |
| 5,064,374 A | * | 11/1991 | Lundgren | 433/173 |
| 5,219,286 A | * | 6/1993 | Hader | 433/172 |
| 5,419,700 A | * | 5/1995 | Sillard | 433/172 |
| 5,554,027 A | * | 9/1996 | Branemark | 433/169 |
| 5,630,717 A | * | 5/1997 | Zuest et al. | 433/172 |
| 5,725,376 A | * | 3/1998 | Poirier | 433/172 |
| 5,779,477 A | * | 7/1998 | Boss | 433/172 |
| 6,056,547 A | * | 5/2000 | Names | 433/173 |

* cited by examiner

Primary Examiner—Cary E. O'Connor
(74) Attorney, Agent, or Firm—Mandel & Adriano

(57) ABSTRACT

A system and method for forming a framework of foundation elements as a component of and foundation for an impression and to support a prosthesis to form a final restoration in a patient. The foundation elements and the prosthesis may be made of the same or similar prosthetic material, or of a metallic or metal alloy material. Each foundation element includes a base member defining a bore therethrough and at least one elongate member extending from the base member. To form the framework, each foundation element is attached to an implant in a patient and a free end of the elongate member is oriented and cut such that it optimally contacts a base member of an adjacent foundation element and is rigidly bonded thereto. A rigid framework is thereby produced which is used to produce the impression. The impression is removed from the patient and a master model is made therefrom. The rigid framework is removed from the impression material and placed along with the master model in an articulator. A prosthesis is molded or sculpted onto the rigid framework and the prosthesis is then attached to the implants in the patient. Final locking screws are placed. The filing and sealing of each of the permanent screws completes the restoration.

10 Claims, 6 Drawing Sheets

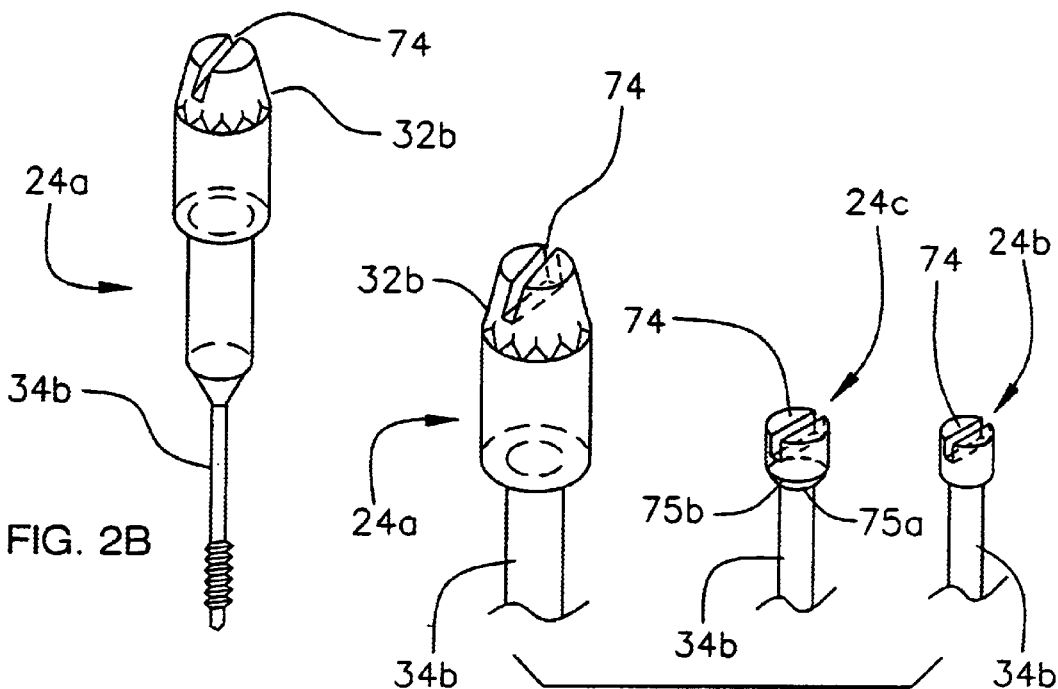
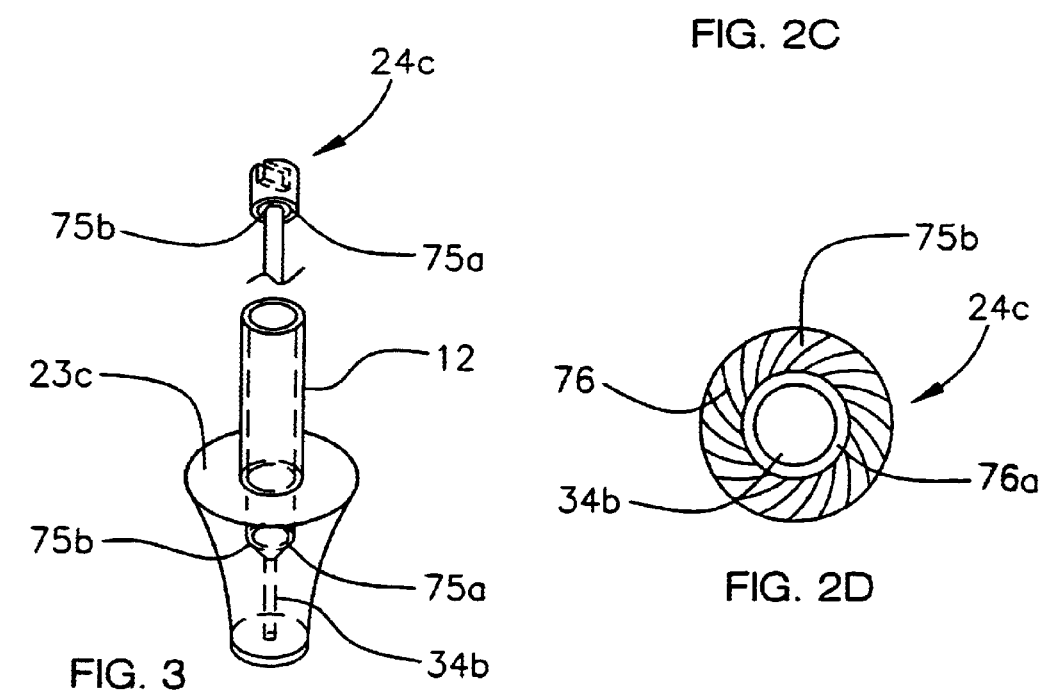

IMPRESSION AND FOUNDATION SYSTEM FOR IMPLANT-SUPPORTED PROSTHESIS

This application is a continuation-in-part (CIP) of U.S. Ser. No. 08/811,494, filed Mar. 5, 1997, now U.S. Pat. No. 6,056,547, the content of all of which are incorporated by reference into the present application.

Throughout this application, various publications are referenced within parentheses. The disclosures of these publications are hereby incorporated by reference herein in their entireties.

FIELD OF THE INVENTION

The present invention generally relates to a system and method for forming a final oral, maxillofacial or cranial restoration consisting of implants, a framework made from individual foundation elements for attaching to the implant and a prosthesis supported on the framework. More specifically, the present invention relates to a system and method for forming a framework for taking an implant impression to more accurately determine the positions and alignment of the implant sites in a patient, and use of the same framework as a support for removable or fixed prostheses to form the final restoration.

BACKGROUND OF THE INVENTION

Osseointegrated implants have been developed as the result of the discovery of the ability of bone to make direct biological attachment to the surfaces of titanium implants. (See Dental Implants: Tissue-Integrated Prosthesis Utilizing the Osseointegration Concept" published in the Mayo Clinic Proceedings, vol. 61 February 1986, pp91–97). An example of osseointegrated. plants is osseointegrated dental implants used as an alternative to a single tooth, fixed bridge or removable dentures to form a final restoration. The procedure involves a first operation to surgically expose the bone and, to drill a hole in the bone where an implant, for example, a titanium anchor element, is to be inserted. An implant having a central aperture temporarily blocked by a covering plug is inserted into the drilled hole in the bone. A flap of skin is then sewn over the site. During the healing period, the bone tissue becomes biologically attached to the titanium implant by growth of the bone tissue.

After the implants have become biologically attached to the bone, the top surfaces of the implants are exposed in a second operation. Sometimes, a metal abutment or "spacer" is attached to each implant as an intermediate between the implant and the framework of the prosthesis, for example when there is a space between the patient's jawbone and the gum tissue above. The description that follows refers to the use of an abutment or spacer.

In order to achieve the desired arrangement of the prosthetic teeth on the implants in the final restoration, a negative impression is made of the patient's mouth which includes the implant sites, and any remaining teeth and gums. One method for making a negative impression involves attaching a temporary stud or a coping to each implant in place of the covering plug. An impression material contained in a dental impression tray is applied around the copings and the dental process. After the impression material cures, the tray with the impression material is then removed from the patient's mouth. The copings are either embedded in the impression material when it is removed from the patient's mouth or reinserted into the impression material after the impression material is removed from the patient's mouth. U.S. Pat. No. 4,693,683 to Lee and U.S. Pat. No. 4,432,728 to Sharkey describe dental trays and techniques for making impressions.

Another method for making a negative impression of the dental process is disclosed in U.S. Pat. No. 5,055,047 to Names. Names discloses a metal impression confirmation system for making an accurate impression for preparing an implant supported dental prosthesis. Individual foundation elements, which are affixed to adjacent elements with a bonding resin, are used to form a rigid metallic framework. An impression is taken of the framework and gums and any remaining teeth. The rigid metallic framework helps to minimize or prevent distortion of the impression material as it cures, and also to prevent distortion of the poured stone for the master model while it cures, to ensure a more accurate molded impression. After the impression material sets, the tray with the impression material and the framework, is then removed from the patient's mouth.

An abutment analog with an aperture and a top surface corresponding to the aperture and the top surface of the abutment attached to the implant is temporarily attached to each coping or foundation element embedded in the negative impression. A positive master stone cast model of the patient's mouth can then be made from the negative impression by embedding the abutment analogs into a material such as gypsum and removing the negative impression by unscrewing the copings or the foundation elements from the abutment analogs. This results in a master stone model that duplicates the location of the implants in the patient's mouth. The positive master model ensures that the prosthesis will match the top of the implants (with or without abutments attached) when the prosthesis is inserted onto the implants in the patient's mouth.

Caps may then be attached to the abutment analogs embedded in the master positive model and a bridge body wax model on the caps, reinforced by a supporting plastic plate, is then produced. The bridge body wax model (the bite template) is placed in the patient's mouth and the caps are screwed onto the abutments. This step checks the accuracy of the impression and determines the height of the bite and the shape of the tooth curvature. After returning the bite template to the master positive model, the positive master model is matched to a positive master model of the opposite jaw and the two positive master models are mounted in an articulator.

In the bite template, teeth of plastic material (acrylate) matching the teeth of the opposite jaw, if any, are attached. The bite template with the teeth is tested in the patient's mouth and then is returned to the master positive model in the articulator. After the positions of the teeth are determined by pre-molding the teeth in soft plastic material, the teeth are removed from the bite template. New wax, connecting the caps on the bite template and built to a suitable dimension, and the caps are then embedded into gypsum. The new wax is melted and removed from the gypsum mold and molten cast gold is poured into the gypsum mold cavity, the caps being embedded into the gold as it sets.

The gold bridge body is removed from the gypsum mold and secured via the caps to the abutment analogs of the master positive model in the articulator. The teeth, the positions of which had been determined by the soft plastic pre-molding, are then attached to the gold bridge body by means of wax. The connection of the gold bridge body to the abutments via the caps is tested in the patient's mouth. If the fit is acceptable, the wax retaining the teeth to the gold bridge body is replaced by plastic material (acrylate) which permanently attaches the teeth to the gold bridge body by means of a pressing method. The gold bridge body with teeth is then screwed onto the abutments attached to the implants via the caps molded in the gold bridge body.

The entire process for preparing a final restoration as described above using fixed implants and a prosthesis involves numerous steps and materials and is tedious and time-consuming. Accordingly, there remains a need in the art for an improved system and method which simplifies the overall process by eliminating some of the steps and materials and thereby decreases the time and cost requirements for preparing the final restoration.

There remains a further need in the art for a system and method for accurately establishing the locations and orientations of the implants and preserving the accuracy throughout the entire process of preparing a final restoration.

There remains yet a further need in the art for a system and method for providing a foundation onto which a removable or fixed prosthesis is attached that is simple to produce, and is readily adjusted to confirm the fit of the prosthesis on the fixed implants.

SUMMARY OF THE INVENTION

The system and method according to the present invention is intended for use not only with dental prostheses but also with oral, maxillofacial and cranial prostheses of other kinds, such as ear, nose and eye socket prostheses, which are supported on foundation elements implanted in bone tissue in a patient. The description of the preferred embodiments are described in connection with dental restorations consisting of prostheses (teeth) which are supported on implants surgically inserted into the jawbone of a patient.

Preferred embodiments of the present invention meet the foregoing needs by providing an impression system that also serves as the foundation for a prosthesis to form the final restoration. The system and method of the present invention provide foundation elements that form a framework for taking an impression for accurate determination of the positions and orientations of the implants and for serving as a foundation on which the prosthesis is supported.

In one embodiment, the system of the present invention comprises individual foundation elements made of a prosthetic material which is similar or the same as the material used to make the prosthesis and is of sufficient strength and flexibility to withstand the stresses and strains transferred to the implant in actual operational environments. The individual foundation elements are attachable to each implant in the patient and bonded together to form a single framework. The framework provides a rigid base around which impression material may be molded. The rigidity of the framework ensures that the molded impression is dimensionally stable.

Each foundation element comprises a base member with a central bore so that a threaded permanent screw can be inserted through the bore and screwed into an implant thereby allowing aligned attachment of the base member to the implant. A final, permanent screw seats on a metal insert collar. The insert collar is located inside the base member with a central bore to receive three screws. The impression screw, the fabricating screw and the permanent screw. The impression and fabricating screws seat on a smooth inside ring. The permanent screw seats on the outer edge ring which contains the anti-rotation mechanism. The bottom of the insert collar is designed to interface with all dental implants. An elongated element extends from the surface of the base member and, when attached to a dental implant, the elongated element extends along the gum line. The opposite free end of the elongated element may be rigidly bonded to an adjacent foundation element with a small amount of a bonding material such as a resinous bonding material. If necessary, the elongated member may be cut to meet the adjacent base member and the bonding material can be added to complete the connection.

After assembly of the framework in the patient's mouth, impression material is injected around the dental process, including the framework, and a dental tray is pressed onto the overcoated framework. The dental tray is provided with openings at locations corresponding to the locations of the impression screws such that the tops of the impression screws extend through the openings. After the impression material has cured, the impression screws are detached from the implants by unscrewing at the tops of the impression screws extending through the openings of the dental tray. The dental tray, the cured impression material mold and the framework of foundation elements imbedded in the mold are then removed from the patient's mouth. The entire assembly is then used to make a master mold using standard procedures.

The master model and a master model of the opposing side of the jaw are placed in an articulator, the relative positions of the upper and lower jaw master models being established by a bite registration. The framework is then removed from the cured impression material mold and attached via fabricating screws to the master model in the articulator. Prosthetic material is then directly molded and sculpted onto the framework to form prosthetic teeth, leaving holes for access to the fabricating and permanent screws.

The final restoration system, comprising the impression framework of foundation elements, the permanent screws, and the prosthetic teeth, is detached from the master model and attached to the implants in the patient's mouth via the permanent pins inserted through the bore of each foundation element. The fit is be confirmed in the patient's mouth and the dentist can make any final adjustments to the prosthesis and if necessary by cutting at one or more specific locations on the prosthesis and reluting the prosthesis. After establishing a satisfactory fit, additional prosthetic material is then applied to the prosthesis to complete the prosthesis. Alternatively, removable dentures may be attached to the framework of the foundation elements via attachments such as ball and sockets and/or bar-to-clips.

In an alternative embodiment, the foundation elements are constructed of a material that can be used for lost wax casting. In this embodiment the foundation elements are joined together to form a framework on the implants in the patient's mouth as described above, and transferred during the impression process to a stone model. The framework is then removed by evaporation or melting to form a metallic framework. This metallic framework is then attached to the implants in the patient's mouth and used to support a prosthesis to form the final restoration.

In addition, the invention provides unshaped pontics that fit over the elongated foundation element to replace missing teeth.

BRIEF DESCRIPTION OF THE DRAWINGS

FIGS. 2A, 2B, 2C and 2D is a side view of a foundation element attached to an implant (2A), shown in partial cross-section, inserted into implants, shown in partial cross-section and the three screws, fabrication, impression and final placement screw, inserted into implants shown in partial cross-section (2A), and details of the impression screw (2B), details of the screw heads (2C) and a bottom view of the permanent screw (2D).

FIG. 3 shows details of the final placement screw and internal seat in the foundation element shown in FIG. 1.

DETAILED DESCRIPTION OF THE INVENTION

Figure 1A:
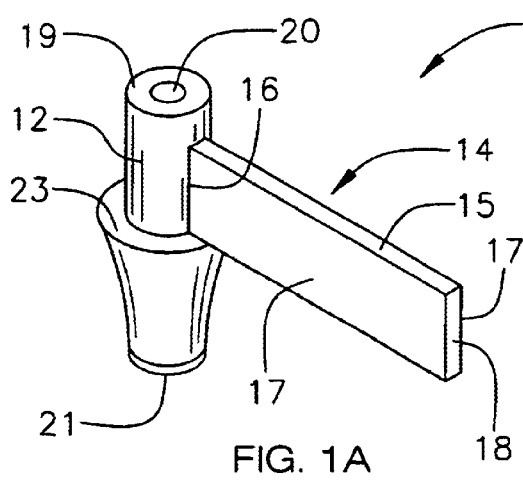
FIGS. 1A and 1B is a perspective view (1A) and a cross section (1B) of a foundation element according to an embodiment of the present invention.

The structure and function of the preferred embodiments can best be understood by reference to the drawings. Where the same reference numerals appear in multiple figures, the numerals refer to the same or corresponding structure in those figures.

Figure 5:
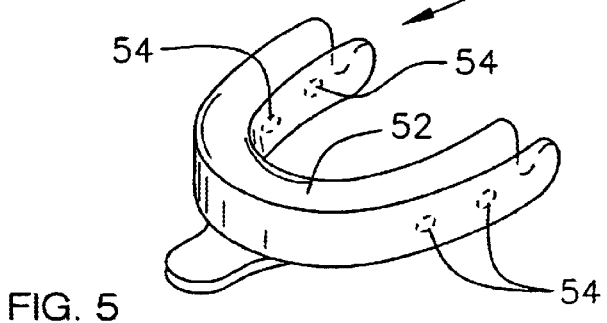
FIG. 5 is a perspective view of a dental tray for making an impression of the dental process.
Figure 6A:
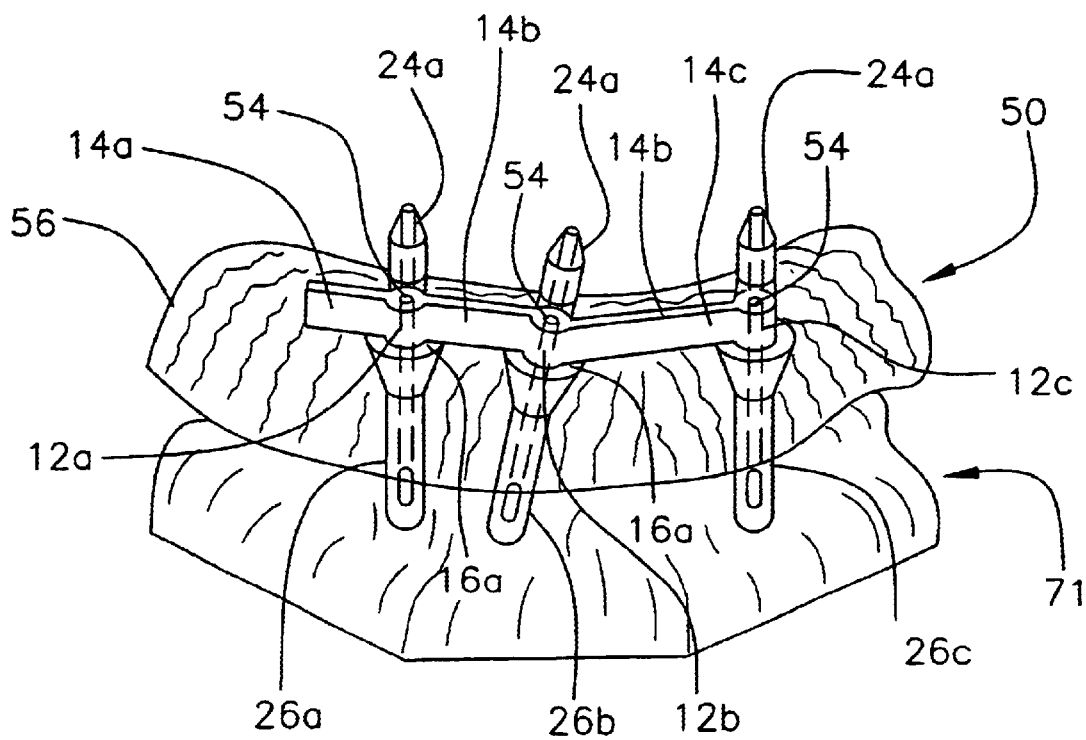
FIGS. 6A and 6B is perspective views of the framework of foundation elements embedded in an impression tray and attached to a stone master model via impression screws screwed into analogs embedded in the model (6A) and 6B is a perspective view of a framework of foundation elements attached to a master model via impression screws screwed into analogs embedded in the stone master model with the impression tray removed.
Figure 6B:
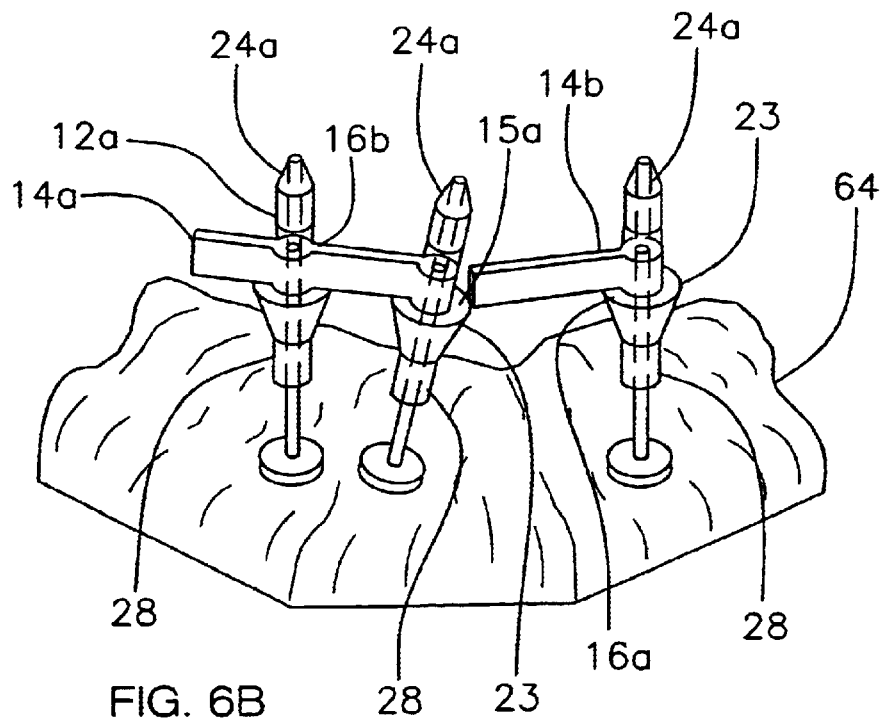
Figure 7:
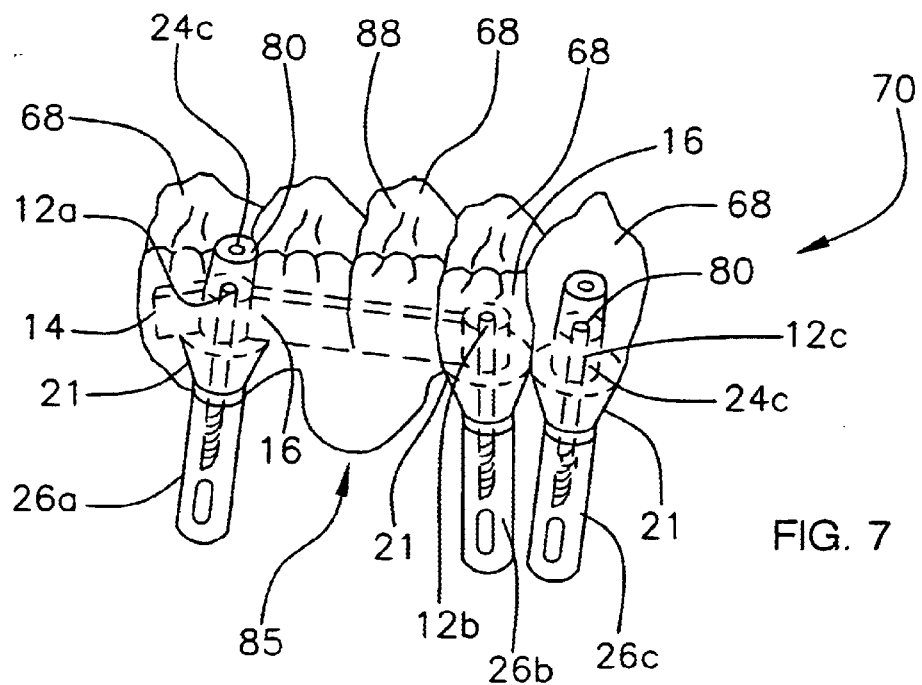
FIG. 7 is a perspective view of a final restoration consisting of a prosthesis supported on a framework of foundation elements attached to the implants.

Referring generally to FIGS. 1–8, the system and method of the present invention comprises generally three stages. The first stage involves attaching foundation elements 10 to implants 26a and 26b embedded in the patient's mouth and connecting foundation elements 10 together to form a rigid framework as shown, for example, in dashed lines in FIG. 7. As shown in FIG. 6A, impression material 56 is applied around the framework thereby embedding the framework in impression material 56, forming a negative impression which includes elements 10 and material 56. Thus, the rigid framework becomes a component of the negative impression of the location of implants 26 in the patient's mouth, from which accurate master model 64 may be made (FIG. 6B). The second stage involves producing master model 64 and placing master model 64 and a corresponding master model of the opposite side of the jaw in an articulator, the relative positions of the master models being established by a bite registration or a bite block, using known procedures (not illustrated in the drawings). After removing impression material 56 from the rigid framework and placing the framework on master model 64 in the articulator, a prosthetic material is molded or sculpted as prosthetic teeth onto the rigid framework, where foundation elements 10 are made of the same or similar prosthetic material. Thus, the framework becomes the foundation supporting prosthetic teeth 68 of final restoration 70 (FIG. 7). The third and last stage involves attaching final restoration prosthesis 70 into the patient's mouth and filling any gaps and holes in the prosthesis with the same prosthetic material. Each of these three stages will be described in further detail below.

As shown in FIGS. 1A and B, foundation element 10 has base member 12 and elongated member 14 extending from base member 12. Base member 12 may be cylindrical, rectangular or any other suitable shape. Base member 12 has top surface 19, bottom surface 21 which flares upward to form seat 23 near bottom surface 21, and defines bore 20, generally perpendicular to elongated member 14. Seat 23 supports the final prosthesis formed around the framework in the final restoration. Bore 20 near bottom surface 21 of base member 12 may be made to be of any shape to match or mate with implants 26 (FIG. 2A) manufactured by different manufacturers.

Elongated member 14 is attached to base member 12 at end 16 and also has top surface 15, opposing surfaces 17 and free end 18. Preferably, elongated element 14 has a generally trapezoidal cross-section with opposing surfaces 17 at a slight taper of at least approximately 2°. Although elongated element 14 may have other cross-sectional shapes, such as a cylindrical cross-section, a generally trapezoidal cross-section has the advantage of providing a flat top surface 15 for receiving prosthetic material for molding or sculpting prosthetic teeth onto foundation elements 10. In addition, this shape ensures a good male-female fit with removable prosthetic teeth such as dentures, if dentures rather than fixed prosthetic teeth 68 are to be attached to foundation elements 10. Foundation element 10 may be of unitary construction or of multiple elements. For example, base member 12 and elongated member 14 may be formed as a unitary element or as two separate components and bonded together, and therefore may be made of the same or different materials such as alumina or zirconium, or similar materials, which are used as a substructure coated with a material such as porcelain and/or fiber re-enforced composite resin.

Figure 1B:
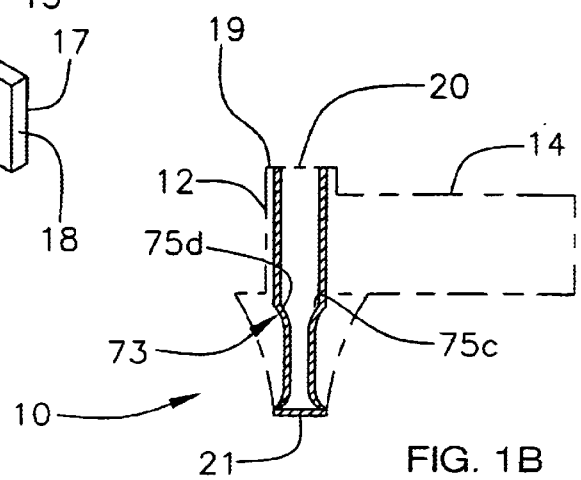
Figure 2A:
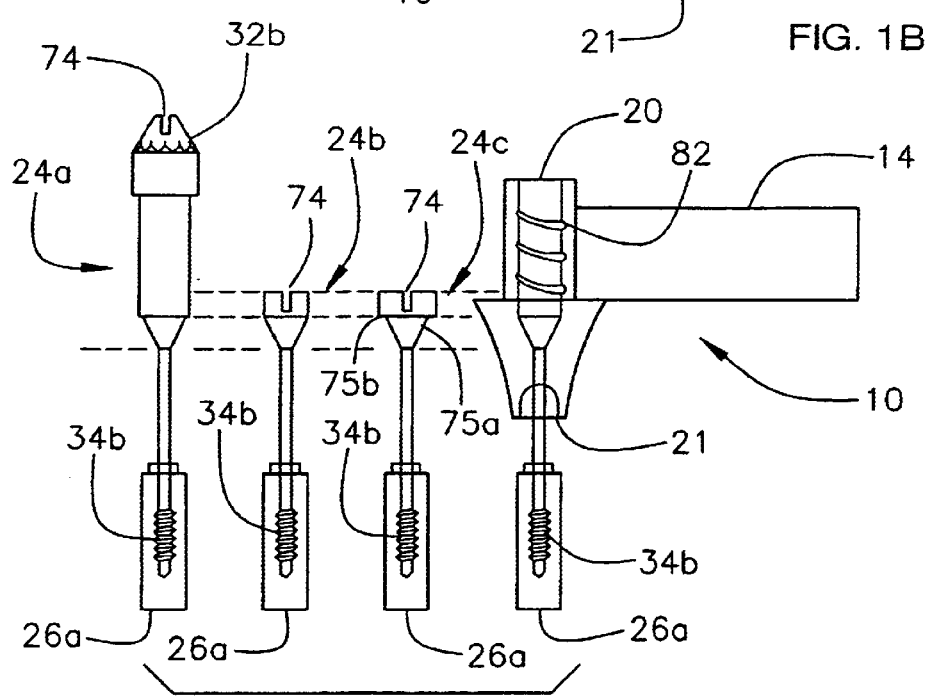

As shown in FIG. 2A, there can be three different screws. The impression screw 24a is used to secure the impression cylinder 12 to the implant 26a. The shape of this screw 24a permits it to be placed and pre-tightened with the thumb and forefinger of the user. The fabrication screw 24b (FIG. 2B) is used only during construction of the prosthesis and for confirming the fit intra-orally. The nature of this "working" screw allows it to seat passively on the smooth surface of the small diameter internal bore 20 of the cylinder 75b, and to be placed and removed repeatedly. The permanent screw 24c has two surface variations on the underside of its head (FIG. 2D) which work in tandem as a sealer and to prevent counterclockwise rotation (75b and 76). The first surface 75a is a hollow area designed to house sealing material such as gold or gold with a binder and/or silicone. The second surface variation is the outer ring 75b which engages the raised metal counter rotation grooves 76 that are located in the seating surface 75c, 75d of the insert 73 (FIG. 1B). This permanent screw 24c is used only once to retain the final prosthesis permanently in place. All three screw heads preferably have a screwdriver slot in the head with a centered square hole 74 to help retain the screw on the screwdriver and to reduce stripping.

Each of the screws, impression screw 24a, fabrication screw 24b and final, permanent screw 24c and threaded plug 80, all have a combination screw/slot top with a square driver placed in the middle and protruding beyond the screw slot 74 (FIGS. 2A, 2B). Square drivers have the advantage of retaining the screw while the professional is working in the oral cavity of the patient. The screw slot favors the application of torque without stripping.

The first stage of the method of the invention involving the process of making an accurate impression of the dental process, where the system of the present invention is utilized as a component of the impression, will now be discussed as can be understood and appreciated by one of ordinary skill in the art.

As shown in FIGS. 1 through 3, to attach foundation element 10 to implant 26a, impression screw 24a with threads 34b is inserted through bore 20 into insert 73 in base member 12 and screwed into implant 26a. Preferably, impression screw 24a has a tapered or round head 32b (FIG. 2A) which provides additional distance from tapered heads of adjacent foundation elements already attached to adjacent implants (see FIG. 6A). Head 32b of impression screw 24a may have a machined internal hexagon, square, circle with a screw slot, combination thereof, or other shape that permits removal with or without the use of a correspondingly shaped tool. Because implants 26a, 26b are rarely implanted perfectly parallel to each other in the bone tissue, due to various factors such as human placement of the implants and jaw and bone ridges, angulation of implants 26a, 26b may result in foundation elements 10a, 10b being angled with respect to each other. Thus, the additional distance provided by tapered heads 32a, 32b allows foundation element 10b to be placed closer to adjacent foundation element 10a without interference between adjacent tapered heads 32a, 32b, even where implants 26a, 26b are at extreme angles toward each other. Furthermore, the additional space provided by tapered heads 32a, 32b also allows easier handling and attachment of foundation element 10b by a dentist or technician.

In a preferred embodiment, foundation element 10 may be made of a biocompatible prosthetic material compatible with the same or a similar prosthetic material used to form the prosthesis to be sculpted or molded directly onto the framework of foundation elements 10. Suitable prosthetic material may be, for example, ceramic optimized polymers, polymer ceramics, polyglass/crystal polymers, or any other suitable material of similar qualities. Ceramic optimized polymers combine the advantages of ceramics (such as strength, durable aesthetic quality, abrasion resistance, and high stability) with the advantage of composites, such as ease of final adjustment, polishability, effective bond with luting composites, low degree of brittleness and susceptibility to fracturing, and ability to repair the restorations in the mouth. One example of ceramic optimized polymers is Targis, manufactured by Ivoclar Williams, composed of fine particle closely packed ceramic fillers embedded in a temperable organic polymer matrix. Targis has enamel-like translucency, fluorescence and hardness, has high flexural strength, and is biocompatible.

Fiber-reinforced composites may also be mixed with a ceramic optimized polymer to produce the material for foundation elements 10 and final teeth prosthesis 68. An example of a fiber-reinforced composite is Vectris, a polymerized fiber/matrix, also manufactured by Ivoclar Williams, which is dentin-colored and translucent, has high strength and high stability, and is biocompatible.

Another material which may be used for foundation elements 10 and final teeth prosthesis 68 is crystal polymers. An example of crystal polymers is Sculpture, manufactured by Jeneric/Pentron, which combines polycarbonate dimethacrylate-containing resins with optically correct glass fillers. The crystal polymer has low water sorption for better color stability and is cured by using a combination of visible light and heat/vacuum.

The foregoing examples of materials which may be used as the material for foundation elements 10 and final teeth prosthesis 68 is merely illustrative and is not meant to be limiting. Any other suitable biocompatible material of similar qualities may be used. A suitable material is to be of high strength sufficient to withstand the stresses and strains which the final restoration system for implant-fixed prosthesis would be subjected to in actual operational environments. The material is also appropriately workable and has enamel-like translucency and hardness, high flexural strength and stability, low degree of brittleness and low water sorption. In addition, the material is cured by any combination of light, pressure, temperature and/or vacuum, biocompatible, and compatible with the interfacing implants and can be effectively bonded with luting composites. Furthermore, while foundation elements 10 and final teeth prosthesis 68 need not be made of the same prosthetic material, prosthetic material for foundation elements 10 must be compatible with prosthetic material used to construct final teeth prosthesis 68.

The advantages of using such materials include that they transfer less stress and strain to the implants in the patient's mouth during use and are aesthetically more like natural teeth. In addition, such materials are easier to manipulate and adjust as described in the system and methods herein.

Referring now to FIG. 6A and FIGS. 4–7 generally, a dentist would first attach foundation element 10a via impression screw 24a to implant 26a which is the implant located furthest back in the patient's mouth, and on the patient's right side if working on the lower jaw and on the patient's left side if working on the upper jaw. The dentist would then attach second foundation element 10b to implant 26b adjacent to implant 26a and continue along in a clockwise or counter-clockwise direction along the patient's gum line in the lower or upper jaw.

After attaching foundation elements 10a, 10b, foundation element 10a is oriented such that elongated member 14a optimally contacts base member 12b of adjacent foundation element 10b, on the side of base member 12b closer to the dentist, as shown by phantom lines in FIG. 7. Because foundation elements 10 are made of a material which can be easily cut and shaped while in place in the patient, elongated member 14a is then cut to a length such that foundation element 10a can be further rotated so that new free end 18a' of elongated member 14a optimally contacts base member 12b of adjacent foundation element 10b and that elongated member 14a extends over a portion of the gum line between implants 26a, 26b.

Alternatively, as discussed above, because implants 26a, 26b are rarely implanted perfectly parallel to each other, angulation of implants 26a, 26b away from each other may result in elongated member 14a being of insufficient length to contact base member 12b of adjacent foundation element 10b. Thus, because foundation element 10 is of a material which can be easily cut by a dentist or technician in a patient's mouth, the dentist or technician may sever elongated member 14a from base member 12a and reattach elongated member 14a via a compatible luting composite to base member 12a such that elongated member 14a is closer to seat 23a or such that elongated member 14a rests upon seat 23a. Alternatively, elongated member 14a may be extended using additional material luted to elongated member 14a so that end 18a optimally contacts base member 12b.

In addition, because adjacent implants 26a, 26b in a patient's mouth may be at different levels, due to various factors such as human placement of the implants and jaw and bone ridges, foundation elements 10a, 10b attached to implants 26a and 26b may also be at different levels. As a result, elongated member surface 15a would not be at substantially the same level as top surface 19b of foundation element 10b. For example, as shown in FIGS. 6A and B, if the level of top surface 19a of a first foundation element extends beyond the level of the adjacent elongated member top surface 15b, top surface 19a may be cut so as to create a slope extending from the level of elongated member 14a to the level of elongated member 14b and thereby creating a continuous surface comprising surfaces 15a, 19a, 15b and 19b. This process may be repeated for all or some foundation elements 10 attached to implants 26.

Figure 4A:
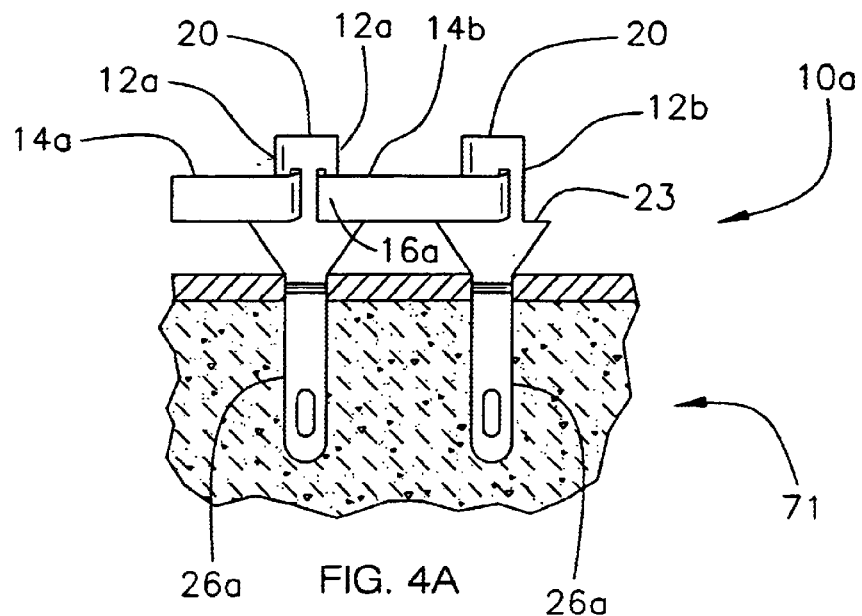
FIGS. 4A and 4B is a side view of two adjoining foundation elements of FIG. 1 attached to two adjacent implants (4A) in a patient's mouth and a top view of the two adjoining foundation elements (4B).
Figure 4B:
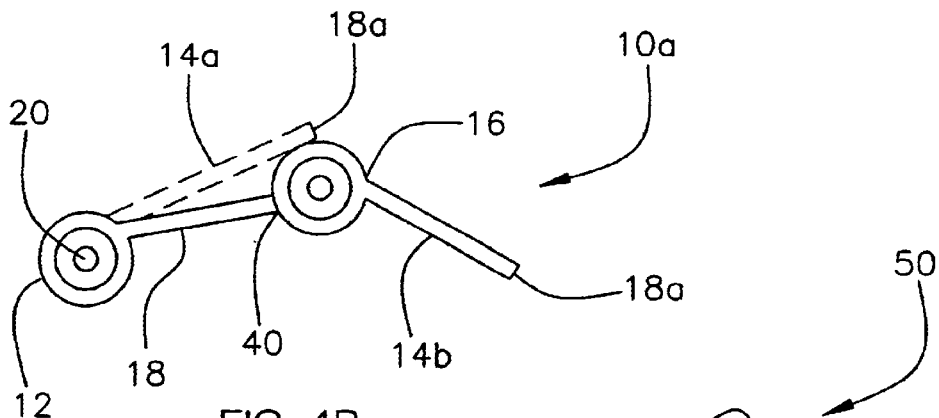

As shown in FIG. 4B, once elongated member 14a is cut and rotated so as to optimally contact base member 12b of adjacent foundation element 10b, elongated member 14a is attached to base member 12b by applying a suitable bonding material such as bonding resin 40 at the interface between elongated member 14a and base member 12b. Bonding resin 40 is selected to be compatible with the material of foundation elements 10 and is preferably a light cured luting composite or bonding resin. After foundation elements 10 have been attached to all implants 26 and bonding resin 40 at all interfaces between base member 12 and elongated member 14 has cured, a single rigid framework is thereby created. Note that elongated member 14 of foundation element 10 attached to the last implant 26 which is the furthest left or the right implant in the patient's mouth, may be cut to a desired length sufficient to support the desired number and size of prosthetic teeth 68 to be attached thereon.

Referring now to FIG. 6A for making negative impression 58, dental tray 50, as shown in FIG. 5 with curved trough 52 and access holes 54 corresponding to locations of implants 26 through which heads 32 of connecting pins 24 extend, is provided. Curved trough 52 is filled with impression material 56. Impression material 56 is also applied areas immediately adjacent to the framework. Dental tray 50 is then pressed against the framework with heads 32 of connecting pins 24 extending through access holes 54.

Impression material 56 is preferably a material that is soft and pliable, such as alginate or other materials of similar qualities. Soft, rather than hard impression material 56 may be used, because the system of the present invention provides a rigid framework around which impression material 56 is applied and thus there is less concern for deformation or distortion of impression material 56. Because soft impression material 56 easily "gives", it is also preferred for taking impressions with the system of the present invention as it produces minimum compression in the gums. Thus, deformation and distortion in impression 58 is minimized or avoided and a more accurate impression 58 of the location of the implants in the patient's mouth is thereby produced.

After impression material 56 has cured, impression screws 24 are unscrewed from implants 26 and analogs 28. Impression screws 24 and impression 58, comprising dental tray 50, cured impression material 56 and the rigid framework embedded in impression material 56, are then removed from the patient's mouth.

Because the rigid framework of foundation elements 10 is embedded in cured impression material 56, the framework preserves impression 58 and thereby minimizes or prevents distortion of impression material 56 as it cures. The molded impression 58 containing the framework is thus sturdy and reliable and may be used as a negative in the construction of master model 64. The relative locations and orientations of foundation elements 10 accurately match those of implants 26. Thus, misalignment of the final restoration prosthesis on implants 26 in the patient is minimized or avoided.

The second stage involving molding or sculpting prosthetic teeth 68 onto the rigid framework of foundation elements 10, while the framework is attached to master model 64 placed in an articulator (FIG. 6B), will now be discussed in detail.

As shown in FIG. 6B, each foundation element 10 is attached to the analog 28, via impression screw 24. Analogs 28 may be those manufactured by manufactures such as Nobel BioCare, ITI or BIOMET or other companies. Master positive model 64 is then made from the impression by embedding analogs 28 into a modeling material such as gypsum. Because impression material 56 completely surrounds the framework of foundation elements 10 thereby providing a rigid and stable negative impression 56, as the gypsum of master model 64 sets, there is no distortion or loss of accuracy of the locations and orientations of analogs 28 in master model 64 which reflect the locations and orientations of implants 26 embedded in the patient's mouth. Thus, a more accurate master model 64 can thereby be produced.

After gypsum 62 has set, impression 58 is removed from master model 64 by unscrewing impression screws 24 from analogs 28. Master model 64 and a master model of the opposite side of the jaw are then placed in an articulator and a bite block or bite registration is used to determine the correct spatial relationship between the two master models (not shown). Impression material 56 is removed from the rigid framework and the framework is placed in the articulator and secured to analogs 28 embedded in master model 64 via fabrication screws 24b. Fabrication screws 24b may provide multiple top interfaces, for example, hexagonal interface and slot-type interface, for compatibility with different tools which may used in screwing fabrication screws 24b.

The framework is prepared for receiving the prosthesis. For example, the surface of the framework is abraded and shaped for accommodating the fixed prosthesis or removable dentures and to form a stable bond therewith.

Prosthetic teeth 68 are then molded or sculpted directly onto the rigid framework such that seat 23 of the foundation element 10 provides support for prosthetic teeth 68. During this stage, prosthetic teeth 68 provides holes for access to fabrication screws 24b such that fabrication screws 24b can be unscrewed from analogs 28 of master model 64 and removed from master model 64 and such that fabrication screws 24b can be screwed into implants 26a and 26b and/or analogs 28 in the model. Thus, the framework of framework elements 10 is the foundation for and a component of the final restoration 70.

The material for prosthetic teeth 68 is the same or compatible with the material used for foundation elements 10. Compatible as used herein means that the materials, in addition to being biocompatible and of sufficient strength and flexibility to withstand stress when located in the final restoration in the patient, cooperate to form a stable bond between the framework and the prosthesis.

The third and final stage involving attaching final prosthesis 70 into the patient's mouth and filling the access holes in prosthetic teeth 68 will now be discussed. As shown in FIG. 7, permanent screw 24c, is inserted through each access hole provided in prosthetic teeth 68 and through bore 20 of each foundation element 10 and screwed into threaded aperture 30 of implant 26 and analog 28. The fit of prosthesis 70 on implants 26 is tested in the patient's mouth. If adjustments need to be made, because foundation elements 10 and teeth 68 are made of a prosthetic material which can be easily cut, the dentist can easily make any necessary final adjustments by cutting and reluting prosthesis 70.

After the fit of prosthesis 70 on implants 26 has been confirmed, a material compatible with the material used for foundation elements 10 and prosthetic teeth 68 is then applied to and thereby sealing any space in bore 20 not occupied by permanent screw 24c and access holes provided in prosthetic teeth 68. The material is then light cured and the final restoration consisting of implant supported prosthesis 70 and implants 26 is complete.

Figure 8:
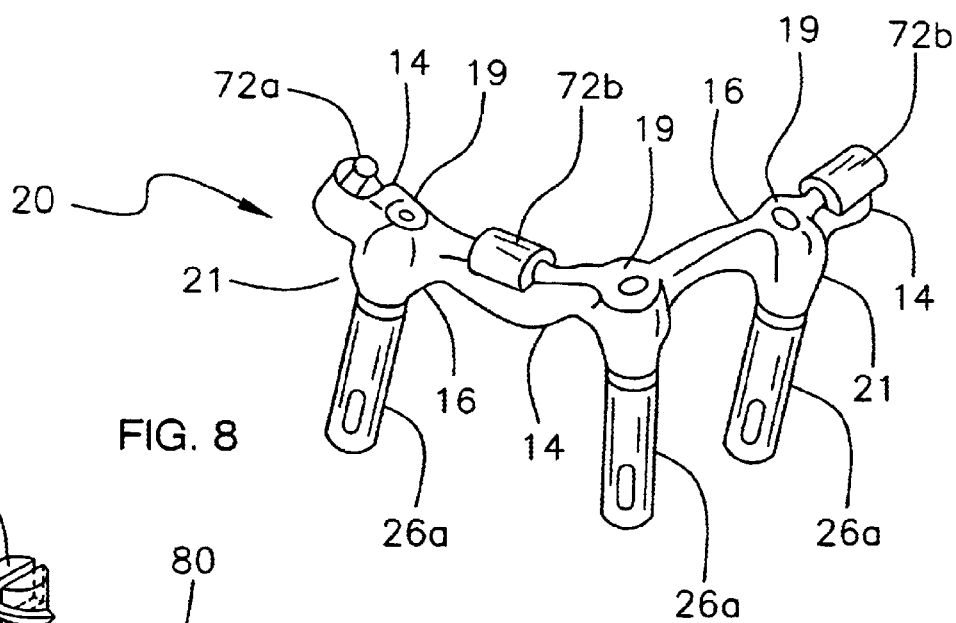
FIG. 8 is a perspective view of the framework foundation elements serving as a foundation for a removable prosthesis in an alternative embodiment of the present invention.
Figure 9:
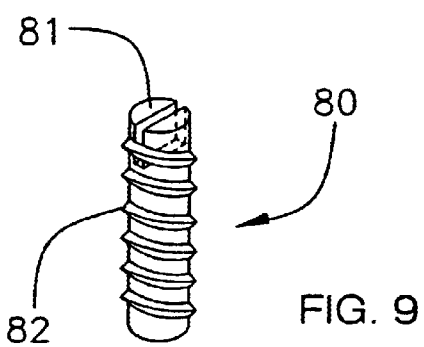
FIG. 9 depicts the reverse threaded filler plug used to fill the access hole over the permanent screw.

Alternatively, as shown in FIG. 8, removable dentures 90, rather than fixed prosthetic teeth 68, may be provided for removable attachment to the rigid framework of foundation elements 10 by addition and/or subtraction of material; such as wax that is subsequently cast into metal (lost wax method) over and around the metal sleeve 21 of the foundation elements. A portion of elongated member 14 may be removed from surface 15 and denture interface 72 may be bonded in place of the removed portion with a bonding resin, such as a luting composite, compatible with foundation elements 10. The interface 72 to secure the dentures on the framework, may be, for example, a ball and joint 72a or of a cylindrical configuration 72b, which is received in a mating recess in the denture, and is generally of a metallic material bonded to the foundation element 10. Prosthetic dentures are typically made of a material, such as acrylic, compatible with the prosthesis material, or composite resins and/or ceramics. These materials can be used to attach the removable dentures to the foundation framework using connecting means such as ball and sockets and/or bar-to-clips.

In an alternative embodiment, the foundation elements 10 can be made of a suitable material such as a plastic material, for example Duralay, which can be evaporated without producing contaminants. In this embodiment, referring to FIGS. 1–8, the framework is constructed of plastic foundation elements 10 on implants 26 which are joined and adjusted for optimal fit on the implants as described above. An impression is then taken as described above, and the impression containing the plastic framework is removed from the patient's mouth. A master stone model is then formed from the impression and having the plastic framework attached, using procedures as described above. Articulation and jaw relationships are also established as described above. A procedure such as lost wax casting is performed, in which the plastic framework is eliminated and replaced with a suitable metal such as gold or metal alloy. The framework can be further modified to have the ideal shape.

Referring to FIGS. 7 and 8, after the framework of foundation elements has been removed from the impression it can be further modified to have an ideal shape (21) to support the addition of tooth colored materials. The modification is accomplished, for example, by reducing foundation elements to create a more natural tooth shape, using a burr or other instrument. In addition, wax or other material may be used to prepare the final shape.

Figure 10:
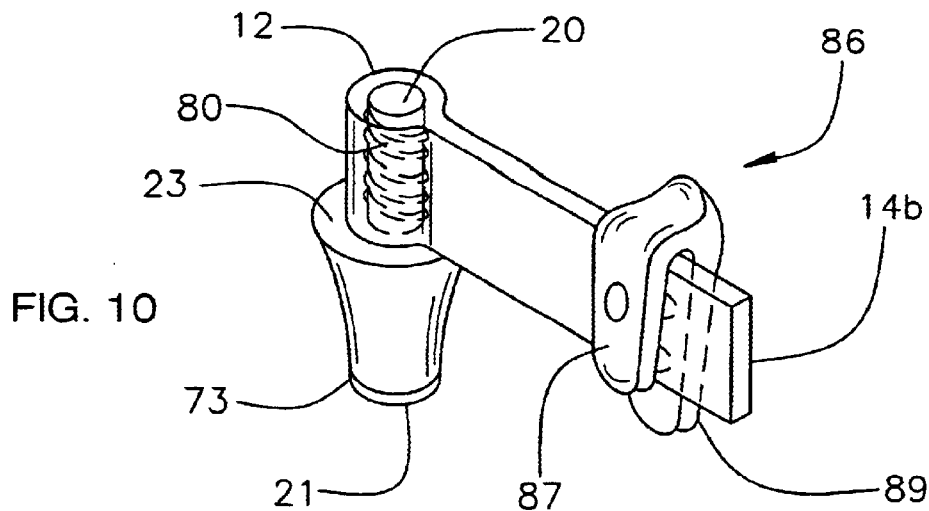
FIG. 10 depicts a movable pontic (false tooth) form positioned on the wing of the foundation element.
Figure 11:
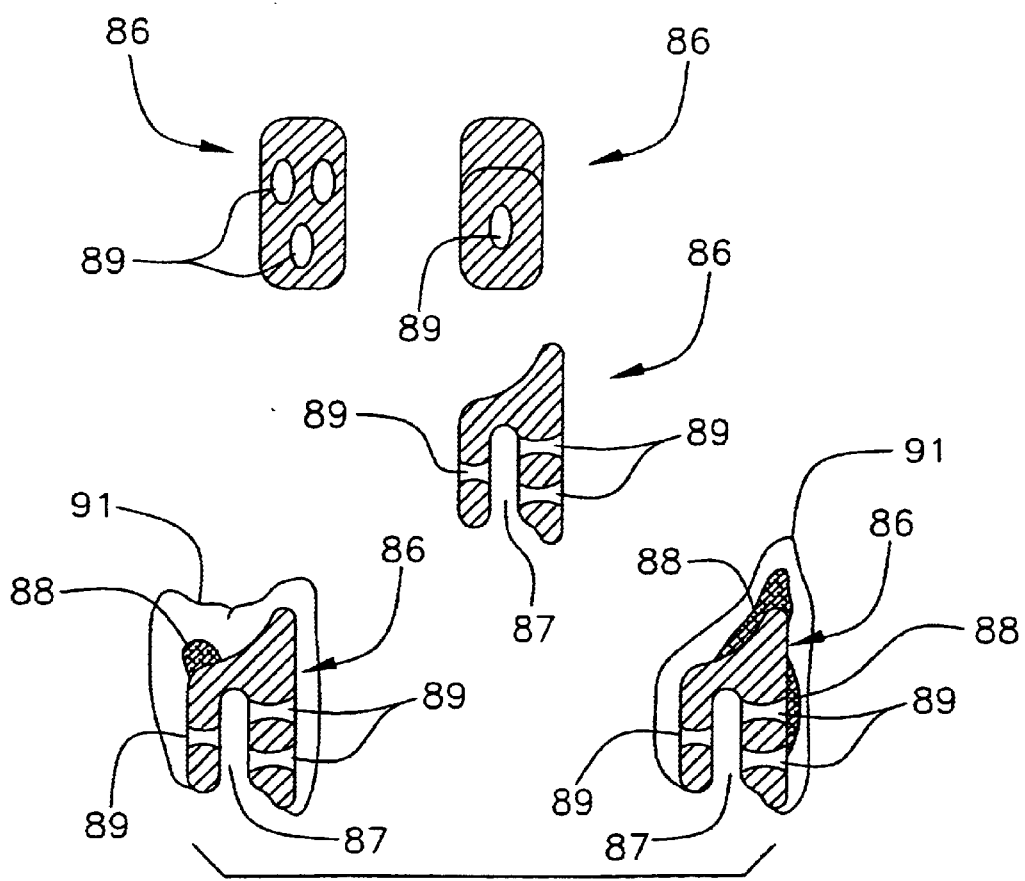
FIG. 11 is views of alternative embodiments of pontics.

A method for quickly providing material for missing teeth in the prosthetic involves the use of tooth shapes or "pontics" as shown in FIGS. 7, 10 and 11. The pontic 85 can be made in the shape of a tooth as part of a bridge. In order to fill spaces of missing teeth in an implanted supported bridge (FIG. 7) an inverted U-shaped pontic unit 86 may be used that fits over the elongated wing extension 14 (FIG. 10) of the foundation element 10 of the invention. There is an opening 87 to permit ideal placement of the pontic unit 86 for appearance and function for the individual patient. The opening 87 is filled between the pontic unit 86 and the wing extension 14 to attach to the foundation element 10. Additional filling material 88 can be used to on the pontic unit 86 to provide additional support for the final tooth colored materials 91 (FIG. 11). Holes 89 may also be made in the pontic unit 86 (FIG. 11) to permit the final tooth colored materials 91 to bond to the pontic unit 86. Another advantage is that there is less expansion and contraction between two similar materials.

The present invention has been described in terms of preferred embodiments. The invention, however, is not limited to the embodiments depicted and described. For example, other materials may be used to form the foundation elements, provided the materials have properties as described herein for supporting the prosthesis and forming the final restoration. Rather, the scope of the invention is defined by the appended claims.

What is claimed is:

1. An implant supported prosthesis system comprising a plurality of foundation elements for attaching to implants in a subject, said foundation elements comprising:
   a) a base member having first and second ends defining an aperture for insertion of a screw therethrough for attaching said base member to an implant; and
   b) at least one elongate member extending from the base member, having a first end at a point of attachment to the base member of an adjacent foundation element, said base member having an internal insert collar for receiving the screw and resting on the top of an implant, and for supporting prosthetic material, wherein said foundation elements are joined together to form a framework for taking an impression of implants in a subject and said foundation elements are used to form the final restoration including the framework and a prosthesis.

2. The prosthesis system of claim 1 comprising impression screws for attaching the foundation elements to implants.

3. The prosthesis system of claim 1 comprising fabrication screws for attaching the impression framework to a master model.

4. The prosthesis system of claim 1 comprising permanent screws for attaching the framework and prosthetic to implants in a subject.

5. The prosthesis system of claim 1, further comprising pontics that fit over the foundation elements to replace missing teeth in a subject.

6. A foundation element for attaching to implants to take an impression of said implants and for supporting final prosthetic material comprising:
   a. base member having first and second ends defining an aperture for insertion of a screw therethrough for attaching said base member to an implant; and
   b. at least one elongate member extending from the base member, having a first end at a point of attachment to the base member and a second, free end that can be cut to optimally contact the base member of an adjacent foundation element, said base member having an internal insert collar for receiving the screw and resting on the top of an implant, and for supporting prosthetic material.

7. The foundation element of claim 6 wherein said base member further comprises a scat to support a final prosthesis on top of implants in a subject.

8. The foundation element of claim 6 wherein said internal insert collar further comprises raised counter rotation grooves on the inner surfaces of said insert collar for retaining a permanent screw connecting said foundation element to an implant in a subject.

9. A method for forming a final biocompatible implant-supported restoration comprising a framework and a prosthesis, wherein said framework comprises a plurality of foundation elements for attaching to implants in a subject, said foundation elements joined together to form a framework for taking an impression of implants in a subject and said foundation elements used to form the final prostheses, comprising:

a. attaching a foundation element via impression screws to at least two implants fixed in the bone of a patient, each foundation element having a base member having first and second ends defining an aperture for insertion of an impression screw therethrough for attaching said base member to the implant, and at least one elongate member extending from the base member, having a first end at a point of attachment to the base member and a second, free end that can be cut to optimally contact the base member of an adjacent foundation element;

b. connecting said free end of each of said elongate members of each foundation element to said base member of an adjacent foundation element thereby forming a framework;

c. taking an impression of said framework on the implants in a patient;

d. removing said impression and framework from said implants in the patient;

e. forming a rigid master mold from said impression and framework and containing said impression and framework;

f. removing said impression material from said framework on said master mold; and g. molding a strong prosthetic material onto said framework, thereby forming a biocompatible implant supported prosthesis, said prosthesis comprising said framework.

10. The method of claim 9 wherein said step of molding prosthetic material further comprises shaping replacement teeth out of said prosthetic material.

* * * * *